United States Patent [19]

Chappelle et al.

[11] 4,385,113

[45] May 24, 1983

[54] RAPID, QUANTITATIVE DETERMINATION OF BACTERIA IN WATER

[76] Inventors: Robert A. Frosch, Administrator of the National Aeronautics and Space Administration, with respect to an invention of Emmett W. Chappelle, Baltimore; Grace L. Picciolo, Fort Washington, both of Md.; Richard R. Thomas, Mountain View, Calif.; Eldon L. Jeffers, LaPorte, Tex.; Jody W. Deming, Annapolis, Md.

[21] Appl. No.: 888,434

[22] Filed: Mar. 20, 1978

[51] Int. Cl.³ .......................... C12Q 1/6; C12Q 3/00; C12Q 1/04; C12M 1/34
[52] U.S. Cl. .......................................... 435/8; 422/52; 435/3; 435/34; 435/38; 435/39; 435/289; 435/291
[58] Field of Search ................. 195/103.5 R, 103.5 L, 195/103.5 M, 127, 139; 422/52; 23/230 B; 435/3, 4, 8, 29, 30, 34, 38, 39, 289, 291, 311, 808

[56] References Cited

U.S. PATENT DOCUMENTS

| | | | |
|---|---|---|---|
| 3,616,253 | 10/1971 | D'Eustachio | 195/103.5 L |
| 3,659,100 | 4/1972 | Anderson et al. | 422/52 |
| 3,745,090 | 7/1973 | Chappelle et al. | 195/103.5 L |
| 3,751,340 | 8/1973 | Witz | 195/103.5 M |
| 3,756,920 | 9/1973 | Kelbaugh et al. | 195/127 |
| 3,797,999 | 3/1974 | Witz et al. | 23/230 B X |
| 3,971,703 | 7/1976 | Picciolo et al. | 195/103.5 L |

*Primary Examiner*—Robert J. Warden
*Attorney, Agent, or Firm*—R. Sandler; J. Manning

[57] ABSTRACT

A bioluminescent assay for ATP in water borne bacteria is made by adding nitric acid to a water sample with concentrated bacteria to rupture the bacterial cells. The sample is diluted with sterile, deionized water, then mixed with a luciferase-luciferin mixture and the resulting light output of the bioluminescent reaction is measured and correlated with bacteria present. A standard and a blank also are processed so that the light output can be correlated to bacteria in the sample and system "noise" can be substracted from the readings.

A chemiluminescent assay for iron porphyrins in water borne bacteria is made by adding luminol reagent to a water sample with concentrated bacteria and measuring the resulting light output of the chemiluminescent reaction. The light output is correlated with bacteria present. A standard and a blank are also processed so that the light output can be correlated to bacteria in the sample and system "noise" can be subtracted from the readings. Modifications may be made in the methodology to differentiate between live and dead bacteria.

An automatic system automatically performs a biolumenscent ATP assay on a concentrated bacterial sample. Reservoirs are provided for the sample, standard and blank. These are sequentially mixed with nitric acid from a reservoir by using two channels of a peristaltic pump. This acid mixture is then mixed with sterile, dionized water from another reservoir using two additional channels of a peristaltic pump and the resulting mixture is then mixed with a luciferase-luciferin mixture from an additional reservoir by employing two more channels of a peristaltic pump. The resulting solution flows through a photometer which indicates the level of the bioluminescent light reaction.

45 Claims, 8 Drawing Figures

RAPID, QUANTITATIVE DETERMINATION OF BACTERIA IN WATER

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435;42 USC 2457) and was also made by employees of the United States Government and may be manufactured and used by or for the Government for governmental purposes without the payment of any royalties thereon or therefor.

BACKGROUND OF THE INVENTION

The present invention generally relates to methods and apparatuses for rapidly making a quantitative determination of bacteria present in water. More particularly, the invention relates to methods and apparatuses for rapidly making a quantitative determination of bacteria present in water such as wastewater effluent, fresh water or sea water by bacterial adenosine triphosphate (ATP) or iron porphyrin assay.

A rapid and routine procedure for a quantitative determination of bacteria present in water is frequently of vital importance, particularly when the determination relates to the quality of a community water supply and a determination is required to be made within a few hours. No prior art technique is capable of giving such a determination in less than a day nor are they suitable for automation.

The present technique for the quantitative determination of bacteria in water, employed for many years, is the colony count, which takes approximately 24 hours to complete. This technique is used for testing wastewater effluent, river or lake bacterial contamination, estuary condition, bay water and the like.

The colony count technique involves the filling of a Petri dish with agar containing a medium considered suitable for the growth of bacteria assumed to be present. Such a medium is trypticase soy agar. *Escherichia coli* is generally the principal coliform commonly found in water contaminated with fecal material. *Pseudomonas aeruginosa* and *Alcaligenes faecalisare* are also commonly found in wastewater effluents. In practice, agar, in powdered form, is mixed with trypticase soy, also in powdered form, with an appropriate amount of water and autoclaved. The broth is then poured out into a number of Petri dishes and allowed to cool until the broth solidifies.

A small sample of the water being tested is streaked on to a dish. This is repeated with a plurality of serial dilutions of the sample in orders of magnitude of 10. With such a procedure a dilution is achieved which is amenable to being counted and at the same time can be related to a given volume of sample.

The colony counting technique is useful with respect to counting bacteria in a salt water environment. Some complications, however, must be taken into account. Sea water supports a great deal of bacteria. However, most bacteria contained in a typical sewage environment are not viable in water with a high saline content, but they are not killed instantaneously. The colony counting technique, therefore, will only confirm how many viable cells are present in the salt water sample that are supported by the particular growth medium employed.

OBJECTS OF THE INVENTION

Accordingly, one object of the present invention is to provide a method to quantitatively determine the presence of bacteria in an aqueous environment.

Another object of the invention is to provide a method to quantitatively determine the presence of bacteria, whether live or dead.

A further object of the invention is to provide a method to quantitatively determine and differentiate the presence of live and dead bacteria.

A still further object of the invention is to provide a method for quantitatively determining the presence of bacteria utilizing the firefly luciferase—ATP assay.

Still another object of the invention is to provide a method for quantitatively determining the presence of bacteria using the luminol—iron porphyrin assay.

Yet another object of this invention is to provide a method to quantitatively determine the presence of bacteria within several hours.

Still another object of the invention is to provide apparatus which automatically makes a quantitave determination.

Another still further object of the invention is to provide a low loss method of concentrating bacteria.

SUMMARY OF THE INVENTION

Briefly, these and other objects of the invention, as hereinafter will become more readily apparent, are attained by bioluminescent or chemiluminescent bacterial assay, either by step-by-step laboratory type methodology or by automated apparatus capable of carrying out the methodology wherein a large fluid sample may be prefiltered to remove most particulate matter, then reduced in volume to concentrate the bacteria present in the large sample. The concentrated sample is then divided into aliquots for either one or both of the bioluminescent or chemiluminescent assay procedures. The bioluminescent assay is made by releasing ATP from the bacteria present in a concentrated sample aliquot, reacting the ATP with an enzyme resulting in a light reaction related to the amount of ATP present, measuring the light and relating the light reading to bacteria present. The chemiluminescent assay is made by reacting a treated concentrated sample aliquot with a luminol solution and measuring the light reaction which is related to the amount of iron porphyrin present, iron porphyrins being present in most bacteria. The light reading is again, as with the bioluminescent assay, related to the bacteria present.

DETAILED DESCRIPTION OF THE PREFERRED EMBODIMENTS

The processes hereinafter described may optionally prefilter particulate matter out of the water undergoing testing. In any event, the particulate matter dealt with is usually very small. Even with the testing of wastewater effluent, the testing is usually conducted after complete treatment of the sewage, i.e., after bacterial degradation, filtration of bacteria and chlorination. A common practice is to prefilter a 10 liter sample through a $10\mu$ filter for macroorganism removal which removes all matter greater than $10\mu$, resulting in the removal of most particulate matter. The particulate matter remains on the filter while most bacteria passes through the filter with the solubles. The criteria applied in determining the filter pore size is that the pore size allow most of the bacteria to pass through yet remove most of the large particulate matter that would interfere with the concentration of bacteria. While the particulate matter may interfere, some bacteria, intended for latter assay, will remain on the filter and this bacterial loss is the "trade-off" to consider. In most cases the prefiltering step will not be employed.

The next pre-assay step, or the first if prefiltering is not employed, is the filter/concentrator step, the purpose of which is to concentrate the bacteria into workable amounts.

Figure 1:
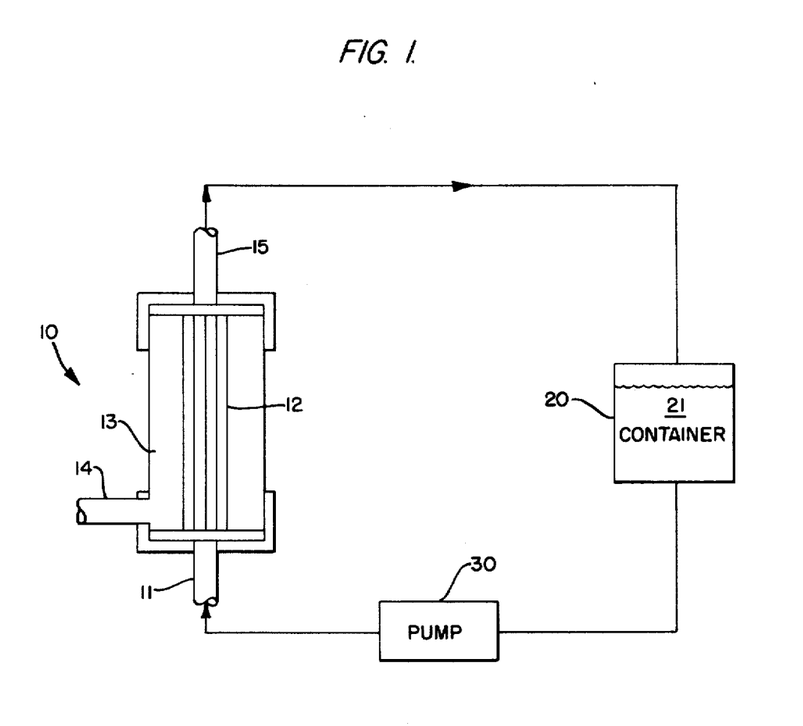
FIG. 1 is a schematic diagram depicting a filter/concentrator configuration used in the present invention.

In the filter/concentrator configuration of FIG. 1, a recirculating mode of performance is shown to concentrate bacteria with minimal loss. This configuration includes a filter 10 of the synthetic polymer hollow fiber concentrator type, such as that manufactured by the Amicon Corporation and designated as their diaflow hollow fiber 50,000 molecular weight cut-off with a total surface area of 10,000 cm$^2$. The surface area may be varied with the size of the filter cartridge to vary the concentration time. Filter 10, while known in the art, has not been used for the concentration of bacteria but rather has been previously used to concentrate macrosolutes and viruses where removal of the particles has been easy. The water sample 21, for example 10 liters, is placed in a container 20 and pumped at approximately 10 psi via a pump 30 to an input port 11 of the filter. The fluid flows under pressure through the synthetic polymer hollow fiber "straws" 12, which are porous, of filter 10. The filtrate then leaks into a general container area 13 and flows out of a filtrate port 14. The bacteria that are too large to pass through the straw pores, continue along the straws, to an output port 15 and back to the container. The continuing filtrate leak-off process results in a continuous volume reduction of the recirculating fluid with a corresponding continuous increase in bacteria concentration. In the recirculating mode it is assumed that there is little deleterious effect from the pressure on the bacteria since the pressure differential on the bacteria is low in a flowing system. The time to concentrate depends on the amount of fluid being concentrated, system pressure, filter porosity, and filter surface area.

Figure 2:
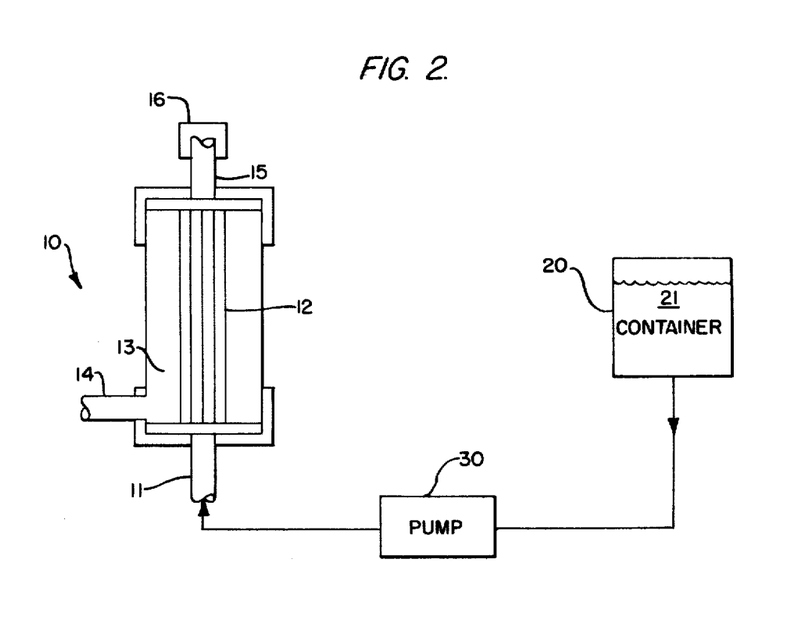
FIG. 2 is a schematic diagram depicting another filter/concentrator configuration used in the present invention.

FIG. 2 illustrates another system for performing the filter/concentration step with the filter 10 in a blocked mode; that is, output port 15 is stopped-up with, for example, cap 16 or a valve. In this mode, there is no recirculation and the only flow is through the pores of the straws. Pump pressure is kept low to avoid affecting the bacteria and to prevent the destruction of the straws. An acceptable maximum is about 15 psi. After all of the sample 21 is forced out of straws 12 and through the filtrate port 14 the bacteria will remain on the inside hollow portion of the straws. To remove the bacteria and form the fluid concentrate, the filter is backwashed under pressure.

The backwashing procedure is accomplished by removing cap 16 and connecting the output port 15 to a pump for a high velocity pressurized air source. At the same time that air is passing through the straws, 100 ml of sterile deionized water is pumped into filtrate port 14 by, for example, a peristaltic pump. The 100 ml with most or many of the bacteria is collected at input port 11. For efficient collection it has been found that a useful procedure is to reconcentrate the 100 ml obtained and to backwash again with an additional 100 ml of sterile deionized water. The principal advantages of this system over recirculation are speed in accomplishing the concentration and an increase in bacterial recovery provided by subsequent backwash steps. It should be noted that the filter/concentration apparatus of FIG. 1 may be run until all of the fluid is removed in the form of a filtrate, and the backwashing procedure may then be employed as with the apparatus of FIG. 2.

The result of using the filter/concentration systems as depicted by either FIG. 1 or FIG. 2 is that there can be realized, by way of example, a reduction of a 10 liter sample to a 100 ml sample, representing a 100 to 1 concentration. The 100 ml portion will contain substantially all of the bacteria originally contained in the 10 liter sample, except those that are lost in the straws and, if used, the prefilter. The amount of loss is assumed to be insignificant.

The resultant 100 ml concentrate is then divided into aliquots for the bacterial assays. Typically a 10 ml aliquot is a minimum volume requirement for each of the bioluminescent and chemiluminescent assays.

The bioluminescent assay is for adenosine triphosphate (ATP) which is a component of all cellular matter, thereby making it a suitable indicator of the presence of various life forms. A very sensitive test for the presence of ATP is an enzymatic bioluminescent assay. The test is basically accomplished by reacting ATP with the firefly luciferase enzyme and luciferin in the presence of a divalent metal ion such as magnesium or manganese.

It has been shown previously that the concentration of ATP derived from several bacteria strains from pure cultures can be closely correlated to a bacterial count. The average ATP content of a bacterial cell has been established at about $3 \times 10^{-10}$ $\mu$g, the range being from $0.28 \times 10^{-10}$ $\mu$g to $8.9 \times 10^{-10}$ $\mu$g.

The ATP assay is accomplished by adding nitric acid at 0.6 N to the 10 ml concentrated sample to rupture the bacterial cells and thereby release the ATP for assay. One unit of the 0.6 N nitric acid is added to 5 units of the concentrate by volume. Under typical circumstances there is no necessity for rupturing and destroying non-bacterial cells prior to assaying bacterial ATP. Certain assumptions are made, i.e., non-bacterial cells will be a relatively small percentage of the cells present and they will be algae, fungi. etc., which will be large enough to be removed during prefiltering, if desired. There may be some non-bacterial cells which, for example, survive the prefiltering step but their number will be insignificant. No need for specificity exists. With respect to soluble ATP, the amount in wastewater is, in many cases, insignificant. Whatever is present will be separated out in the filter/concentration step by the hollow fiber concentrator and will pass with the filtrate.

After rupturing the cells with acid the sample is diluted with sterile deionized water on a one-to-one basis by volume. The purpose of this step is to minimize the inhibitory effect of the acid on the luciferase with which the ATP is react. If there is more than a one-to-one dilution the sensitivity of the reaction is affected; if there is less, the acid is too inhibitory.

The next step is to inject 0.1 ml of the treated sample into 0.1 ml of the luciferase-luciferin preparation. The injection procedure takes place in a light-tight cell of a photometer employing a photo-multiplier tube. (The luciferase solution is prepared with hydrated luciferase-luciferin with 0.25 M TRIS, 0.01 M $MgSO_4$ and 0.001 M Clelands reagent). There is a light reaction related to ATP of which most is bacterial ATP. Further, this procedure is considered an assay of live bacteria because, in most cases, substantially all of the ATP in a bacterial cell hydrolyzes upon death of the cell.

At this point it must be realized that all that has been obtained is a light reaction related to ATP present. To have the light reading from the ATP in the sample correlated with a known amount of ATP, a standard must be processed with a known amount of ATP. This is done by taking a known amount of pure dehydrated ATP and diluting it to an appropriate concentration in water, e.g., 0.1 $\mu$g ATP/ml $H_2O$ and adding 0.6 N nitric acid in a 6:1 ratio by volume. The resulting mixture is mixed 1:1 with sterile, deionized water and injected into the luciferase-luciferin mixture in the photometer. To establish a threshold for system "noise" which accounts for part of the light reading, a blank must be processed. The blank involves mixing sterile, deionized water in a 6:1 ratio with 0.6 N nitric acid, then 1:1 with water and injecting it into the luciferase-luciferin mixture. The standard and the blank, therefore, are processed exactly like the bacteria containing sample.

In practice, once the blank and standard light reading are obtained, the blank reading is subtracted from both the standard and the sample readings. Since the standard reading is usually very high and the blank reading very low, it is not important to subtract the blank reading from the standard. However, since many sample readings are low, the blank reading is subtracted from those. When the subtraction process is completed, the determination of bacteria in the sample is made through proportionality with the standard since the readings are linear. (The limits of the instrument set the working limits, and the reagents, including enzyme, are adjusted so that a linear relationship is maintained).

In turn, the chemiluminescent assay is for iron porphyrins which are protein molecules with an iron center. Iron porphyrins are contained in bacteria, dead and alive, and in solution. The luminol reagent is $2.5 \times 10^{-4}$M luminol (5-amino-2,3-dihydro-1,4-phthalazinedione), 0.1% $H_2O_2$, $6.33 \times 10^{-3}$M EDTA (ethylene diamine tetraacetic acid), 0.75 N NaOH. 0.15 ml of a water sample is injected into 0.15 ml of the luminol contained in the light tight reaction chamber of a photometer, and the light measured. Again, the reading is meaningless without a blank and a standard being developed and read. The blank is deionized water and the standard is a known amount of bacteria in the deionized water. To develop the standard, bacteria must be grown in a broth, for example, trypticase soy broth washed in deionized water and the total bacteria count established using an electronic particle counter such as a Coulter counter. The light reading using this basic procedure is related to iron porphyrins contained in both live and dead bacteria and in solution as well as to metal ions present.

Several slight modifications may be made in the basic procedure to obtain different component readings. For example if a six second delay is made between injecting the sample into the luminol reagent and taking the light reading, the reaction due to the presence of metal ions, which is short lived, is eliminated, i.e., the light reading will represent iron porphyrins in live and dead bacteria plus the iron porphyrins in solution. The explanation for this is that the luminol reaction is fast for inorganic ions but slow with respect to organic reactants. Another variation is to pretreat the sample will enough added hydrogen peroxide to reach a 0.5% $H_2O_2$ solution. Since reagent grade is normally 3% this means a six-fold dilution of the 3% solution is required. This hydrogen peroxide pretreatment apparently breaks the protein ring of the soluble iron porphyrins and frees iron as a molecule. While iron in solution gives a light reaction with luminol it is not nearly as high as with the iron porphyrins in solution and, therefore, the false signal, i.e., the signal from non-bacterial sources, is substantially lowered. In other words by combining the hydrogen peroxide pretreatment and employing the six second delay in taking a light reading with the luminol reaction, the reading taken will substantially represent only those iron porphyrins from live and dead bacteria.

One other pretreatment, which is be accomplished independently since it may be incompatible with the hydrogen peroxide pretreatment, is carbon monoxide (CO) bubbling. CO bubbling results in a loss of signal from viable cells, i.e., the only light reaction obtained is that from dead cells, and soluble iron porphyrin (and metal ions later removed by time delay). The technique employed is to bubble CO through the cell suspension at a rate sufficient to produce a steady stream of bubbles.

It is assumed that luminol reacts with oxidized iron porphyrins in the bacterial cell. In the presence of hydrogen peroxide all reduced iron porphyrins are immediately oxidized and luminesce with luminol. Many iron porphyrins, such as the cytochromes, are reversible and, in an actively metabolyzing cell are continuously undergoing oxidation-reduction reactions. In a dead cell, where no metabolic activity is taking place, all of the iron porphyrins are assumed to be in the oxidized state as a result of the normal chemical equilibrium. With the bubbling of CO in a bacteria suspension, it appears that much, if not all of the iron porphyrins in the live cells become reduced and complex with CO.

The luminol assay appears, therefore, to respond to a CO treated bacterial sample in the following manner: (1) the luminol reacts with the oxidized porphyrins in the dead cells, (2) no luminol reaction occurs with the reduced porphyrin—CO complex in the live cells.

In summary, when the basic luminol test is made, the light reaction relates to iron porphyrins in live and dead bacteria and in solution. With CO bubbling the light reaction relates to iron porphyrins in dead bacteria and in solution. In the case of the $H_2O_2$ pretreatment, the light reaction relates to iron porphyrins in live and dead bacteria. In all cases the reaction from metallic ions is eliminated with the six second delay. It should be understood that if the filter/concentrator previously described is used, the soluble iron porphyrins are essentially removed in the filtrate. With the above-noted relationships known, readings may be taken from which can be determined the amounts of live and dead cells present. For instance, assuming the filter/concentrator is employed and the soluble iron porphyrins are removed, the basic luminol reaction will give the total of live and dead bacteria present. The luminol reaction will give the dead bacteria present when CO bubbling is employed. Subtracting the latter reading from the former enables a determination of the amount of live bacteria present.

The prior discussion has centered on the assay of bacteria which are viable in fresh water and to a lesser extent, the assay of such bacteria in salt water. The methods previously described are not useful for recovery of salt water bacteria (and phytoplankton) because these microorganisms appear more fragile than fresh water bacteria which apparently are destroyed under pressure and, additionally, are damaged by the replacement of sea water with a backwash of fresh water in the filter/concentrator. Thus, concentrations for both the bioluminescent and chemiluminescent assays of sea water-borne bacteria (and phytoplankton—the assays here are really not bacterial, they are biomass assays) can not use the previously described filter/concentrator. In the case of either assay, the concentration can be accomplished with a vacuum-membrane filter by flowing, for example, 1 liter of seawater through the filter. The bacteria and phytoplankton remain on the filter. The typical filter employed has a 0.22 micron pore size and a 45 mm diameter. Both the salt water bacteria and the phytoplankton contain ATP and iron porphyrins. In the case of an ATP assay, the filter is washed in 10 ml of 1.0 N $HNO_3$ with the result that the ghosts are substantially left on the filter membrane, i.e., the cells are ruptured and the soluble ATP passes through the filter. The resulting solution is diluted 1:20 in sterile, deionized water to minimize the inhibitory effect of the nitric acid on the luciferase. At this point the method is the same as previously described for an ATP assay of fresh water bacteria, i.e., 0.1 ml of the sample is injected into 0.1 ml of a luciferase-luciferin solution in the photometer and the light reading taken. Again a standard and a blank must be developed. The standard is developed by passing 0.1 μg ATP/ml 10 ml of 1.0 N $HNO_3$ through a filter wetted with sample filtrate, diluting and assaying as before. The blank is the filtrate of the salt water sample, refiltered and followed by nitric acid extraction.

For the chemiluminescent assay using luminol, the bacteria and phytoplankton are again separated on the same vacuum-membrane filter as described above. The bacteria and phytoplankton are then washed with, for example, 10 ml of a 0.1 N NaOH—50% ethanol mixture. The ghosts are left on the filter and the iron porphyrins are washed into solution. Thereafter 0.15 ml of the solution is injected into 0.15 ml of the luminol reagent (the luminol reagent is the same as that described as used with the fresh water bacterial assay) contained in the photometer. The light reading is then taken. A standard and a blank must again be developed and taken. The standard, catalase, while not representative of all iron porphyrins present in an organism, at least provides a suitable reference point. The standard, in this case, is developed by adding a known amount of catalase (an iron porphyrin) to the 0.1 NaOH—50% ethanol solution. The blank is the filtrate of the salt water refiltered followed by extraction with the 0.1 NaOH—50% ethanol solution. It is possible that the six second delay in measurement may be eliminated because most of the interfering substances are removed in the filtrate.

Figure 3:
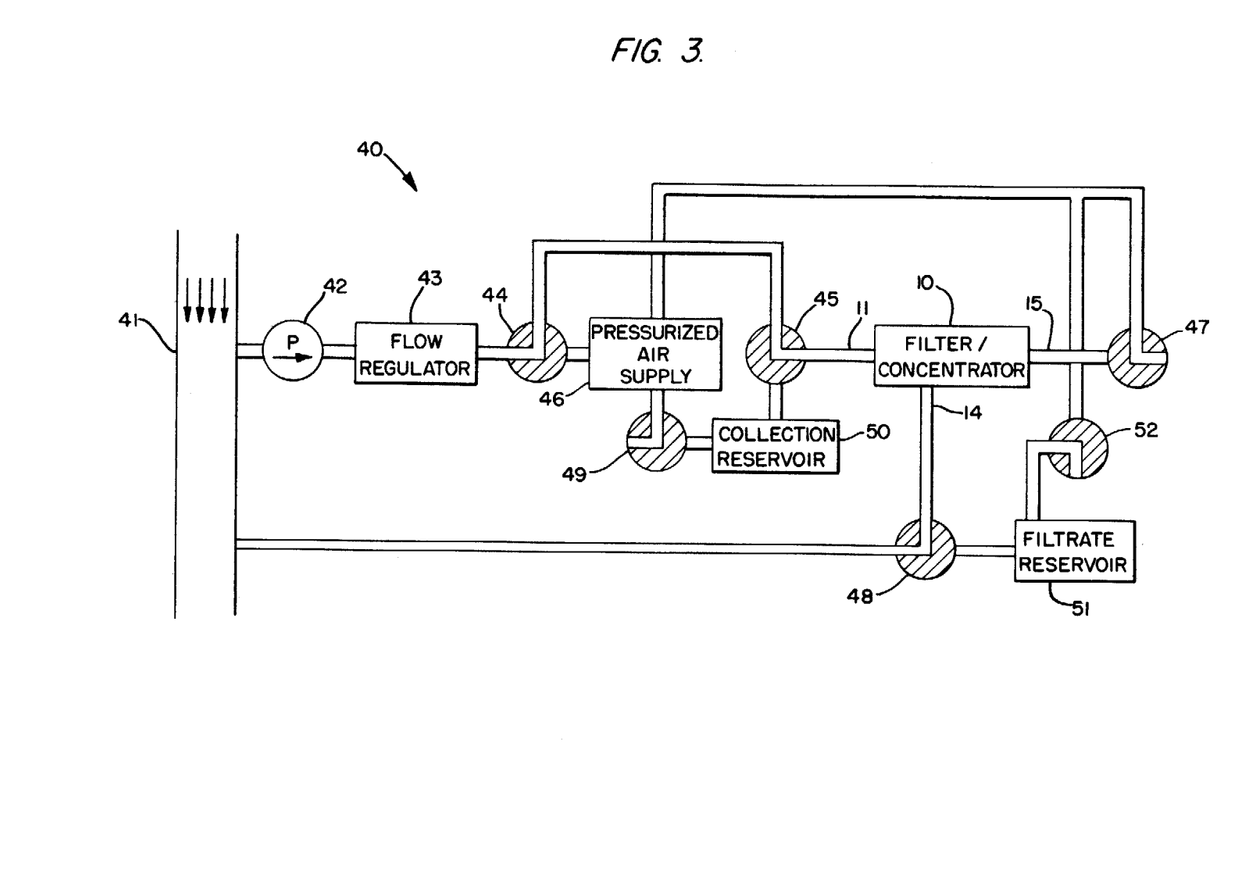
FIGS. 3, 3A, 3B and 3C are block diagrams depicting various operational sequences of an automated filter/concentrator configuration used in the present invention.

FIGS. 3, 3A, 3B and 3C illustrate the various sequences of operation of a system configuration 40 for automatically and periodically sampling a fluid, for example, wastewater effluent, and collecting the bacteria contained in effluent in a concentrated sample, i.e., a reduced volume. FIG. 3 illustrates the system 40 in a sequence whereby the volume of the fluid sample is reduced to zero leaving bacteria contained in the sample on the inner surfaces of the hollow fibers of a filter/concentrator as previously described. It should be understood that the systems described may be subject to computer control in practice. The system completes an assay cycle every two hours. In the FIG. 3 sequence of operation, a pump 42 pumps out effluent contained in a conduit 41 at a rate of greater than 100 ml/min, i.e., taking a minimum 100 min to pump a 10 liter sample of effluent. A flow-regulator 43 regulates the rate of flow, for example, to 100 ml/min. A valve 44 is open to a valve 45 and is closed to a pressurized air supply 46 which is at about 15 p.s.i. Valve 45 is open to the filter/concentrator 10 at input port 11 and closed to a collection reservoir 50. A valve 49 is in a position to cut off the pressurized air supply 46 from the collection reservoir 50. A valve 48 is directly open to the wastewater effluent conduit 41 to normally drain off the filtrate coming out of filtrate port 14 while a valve 47 blocks the output port 15. During the drainoff period valve 48 is switched open to filtrate reservoir 51 for one minute until 100 ml of filtrate is collected. A valve 52, connected to pressurized air supply 46, is closed to filtrate reservoir 51. The effect of operation in this mode is that the effluent is being forced into the filter/concentrator 10, the liquid phase is being forced out filtrate port 14, and the bacteria and other sufficiently large solid phase particles remain in the straws.

Figure 3A:
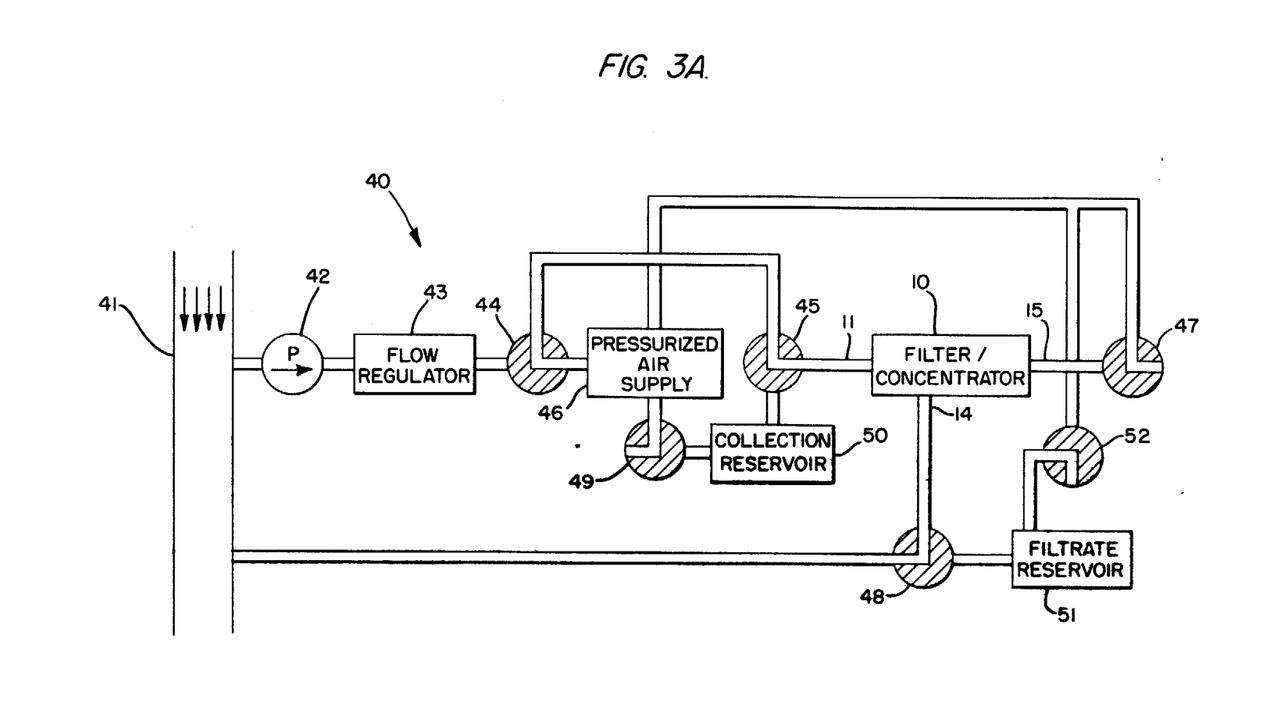

FIG. 3A shows the sequence of operation of the automatic fluid sampling system after operation of the system in the FIG. 3 configuration, i.e., after 100 minutes of operation, with the result that bacteria are collected on the inner surfaces of the straws and 100 ml of filtrate is collected in the filtrate reservoir 51. The purpose of this step is to remove the effluent still in the lines and the filter/concentrator 10.

Pump 42 is either shut off or if effluent is required for other purposes, diverted (not shown) from the flow regulator 43. Valve 44 is rotated a quarter turn clockwise to connect the pressurized air supply 46 to the filter/concentrator 10 through valve 45 for a sufficient time, for example, two minutes, to substantially blow any fluid remaining in the lines and the filter/concentrator 10 out the filtrate port 14.

Figure 3B:
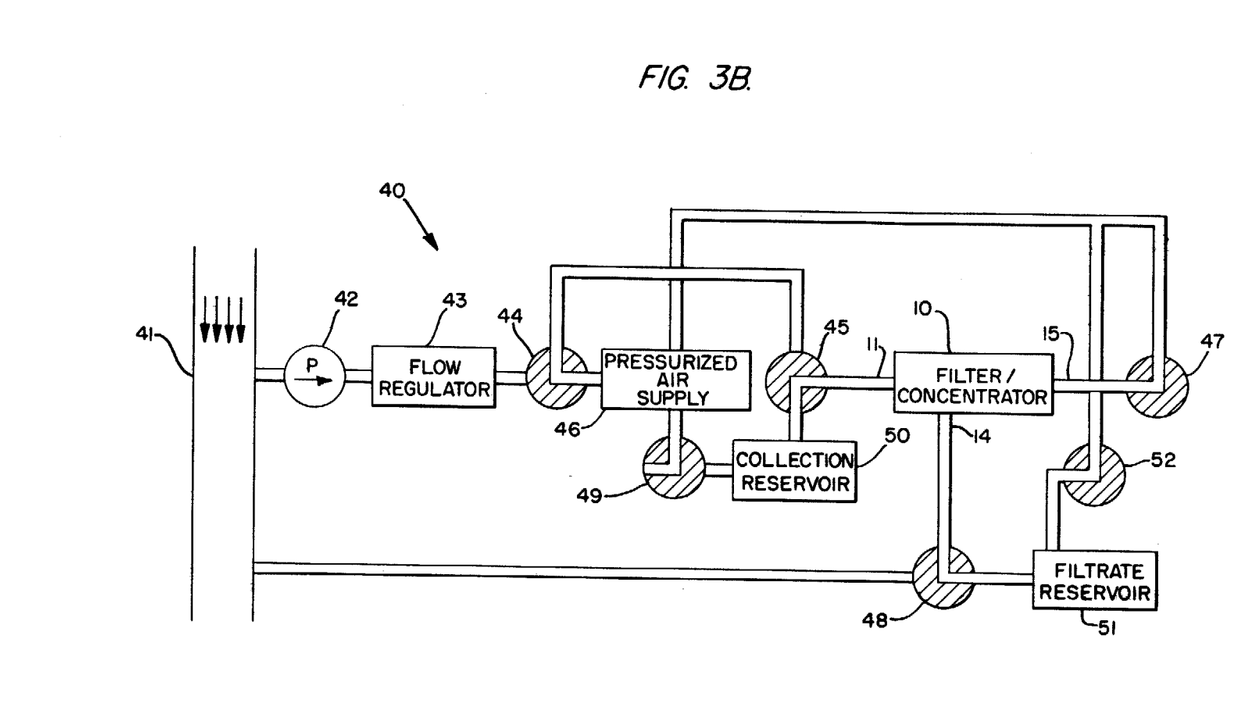

FIG. 3B shows the system configuration for the backwash sequence of operation which generally involves the use of the filtrate to flush the bacteria collected and concentrated in the straws from the original 10 liter sample. For this operation, valve 44 is left in place, valve 45 is turned a quarter-turn clockwise to connect the collection reservoir 50 to the filter/concentrator 10, valve 48 is turned a quarter-turn clockwise to connect the filtrate port 14 to the filtrate reservoir 51, valve 47 is turned a quarter-turn counter-clockwise and valve 52 is turned a quarter turn clockwise to connect the pressurized air supply 46 to the filtrate reservoir 50 and the output port 15, respectively. The result of this configuration is to continue blocking the effluent while forcing filtrate into filtrate port 14 and pressurized air across the straws from the output port 15 in order to collect the bacteria with filtrate off the straws and into collection reservoir 50.

Figure 3C:
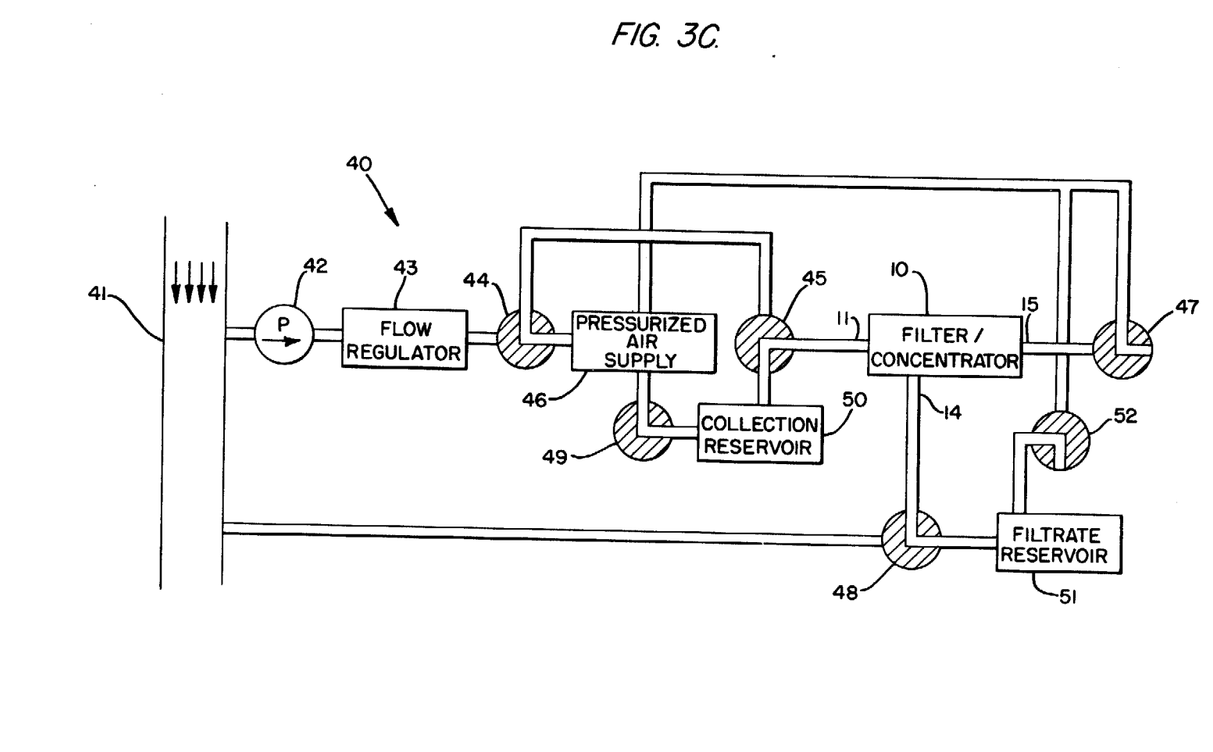

FIG. 3C discloses the reconcentration system configuration whereby the concentrate in collection reservoir 50 as a result of the backwash mode of FIG. 3B is forced into the filter/concentrator, to again deposit bacteria on the inner surfaces of the straws of the filter/concentrator 10. In the configuration of FIG. 3C, valves 44, 45 and 48 are left in their prior position while valve 49 is turned a quarter-turn clockwise to connect the pressurized air supply 46 to the collection reservoir 50. Valve 52 is rotated a quarter-turn counter-clockwise and valve 47 is rotated a quarter-turn clockwise in order to cut-off the pressurized air from the filtrate reservoir 51 and the output port 15, respectively. The air pressure then clears the lines and filter/concentrator 10 of any remaining fluid.

The FIG. 3B and FIG. 3C cycles are repeated several times. The objective of cycling these two modes, i.e., backwash and reconcentration, is to remove more bacteria from the straws than would be possible with a single cycle thereby to improve the effective bacterial recovery. However many times the cycle is repeated, the FIG. 3B cycle should be the last since the overall objective is to obtain a concentrated sample in collection reservoir 50. It should be understood that the collection reservoir 50 will be tapped by as many fluid lines (not shown) as necessary to connect it to the assay systems present. In this instance there are two assay systems, one a bioluminescent assay for ATP and another a chemiluminescent assay for iron porphyrins employing luminol. As previously stated, the sequences of operation necessary to complete the bacteria concentration cycle can be completed in about two hours.

Figure 4:
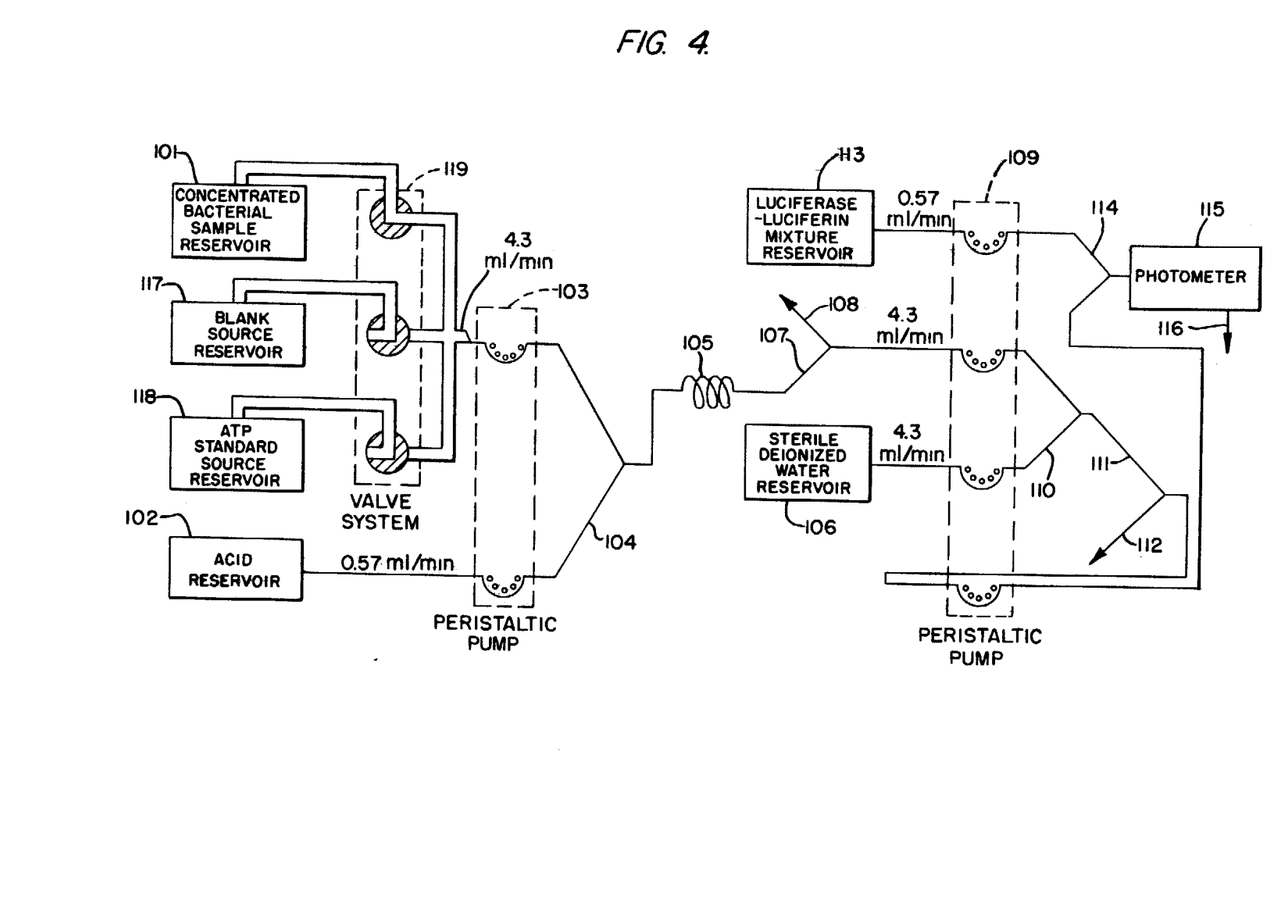
FIG. 4 is a block diagram depicting the automated ATP assay configuration of the invention.

FIG. 4 discloses an embodiment of an automatic system for carrying out a bioluminescent assay of bacterial ATP in a fluid. In this system a concentrated bacterial sample source reservoir 101, a blank source reservoir 117, and an ATP standard source reservoir 118 are all connected to one channel of peristaltic pump 103 via valve system 119. These three sources are sequentially switched into the overall system for individual ATP assay. The fluid in the concentrated bacterial sample source reservoir 101 is drawn from the concentration reservoir 50 as shown in FIG. 3B after completion of the last cycle. The blank source is the filtrate 117 drawn from the filtrate reservoir 51 as shown in FIG. 3B after completion of the last cycle. The ATP standard source 118 is a laboratory developed reagent consisting of 0.1 $\mu$g ATP/ml. It should be understood that the system maybe continuously running or operated periodically.

The blank source 117 is normally assayed first by being switched into the system via valve system 119 which allows the peristaltic pump 103 to begin drawing the fluid. Simultaneously the peristaltic pump is drawing 0.6 N nitric acid, via another channel, from the acid resevoir 102. The speed of the pump and the diameter of the tubing connecting the fluid sources to the pump are carefully designed to allow the fluids being assayed to flow at the rate of 4.3 ml/min. and the acid to flow at the rate of 0.57 ml/min. The output of the pump is combined through a "Y" junction connector 104 and then placed through residence coil 105 which may be a tube the length of which is cut so that at the combined flow rate of 4.3 ml/min. and 0.57 ml/min. the fluid will remain mixed for a period of 60 seconds prior to entering peristaltic pump 109. The mixed fluid is placed first through a "Y" junction connector 107 with one leg 108 open to drain off 0.57 ml/min. Accordingly, 4.3 ml/min. is entering one channel of peristaltic pump 109. A reservoir of sterile deionized water 106 is, at the same time, also being pumped out at the rate of 4.3 ml/min. by another channel of the pump 109. The flow from the residence coil 105 and the deionized water reservoir 106 is combined, with a combined flow rate of 8.6 ml/min. at the "Y" junction connector 110 and thereafter, placed through "Y" junction connector 111 with drain leg 112 left open to drain off all but 0.57 ml/min. of the combined fluid. This fluid is fed back to another channel of peristaltic pump 109 and combined, through another "Y" connector 114 with the flow from still another channel of pump 109 which connects to reservoir 113, containing a luciferase-luciferin mixture. This mixture is firefly luciferase-luciferin powder and 3 ml. of 0.25 M TRIS, 0.001 M Cleland's reagent, and 0.01 M MgSO$_4$ at a pH of 8.2. Exemplary procedures for making luciferase and luciferin are described in U.S. Pat. No. 3,745,090. Both luciferase and luciferin are available from E. I. Du Pont de Nemours and Co. (Inc.), Wilmington. Del. The output of "Y" connector 114 is placed into photometer 115 for a continuous reading. The flow through the photometer is drained off through the photometer drain 116. The system described, therefore, employs the concentrated bacterial sample source, the blank source and the ATP standard source and completes an ATP assay for each in terms of a photometer reading. It does this by mixing either the sample, the blank or the standard with nitric acid, allowing the mix to remain long enough to rupture any bacteria present, to free the bacterial ATP. It then mixes the acid mix with sterile, deionized water to lessen the inhibitory effect of the acid on the luciferase. The resulting mixture is then mixed with the luciferase-luciferin mixture to achieve a bioluminescent reaction proportional to ATP present. The reaction is measured by the photometer. The system operates similarly with respect to the standard and the bacterial sample, which are switched in after the blank is assayed.

The photometer reading for the blank is subtracted from the photometer readings for the standard and the sample. (The standard reading is usually so high compared to the blank, that the blank need not be subtracted from the standard.) The light units for the standard are then compared with the light units for the sample minus the blank on a simple ratio relationship to determine the ATP present in the sample. The ATP in the sample can then be related to bacteria in the sample using a factor that represents the average ATP content of a bacterial cell, i.e., $3 \times 10^{-10}$ $\mu$g ATP/cell.

Figure 5:
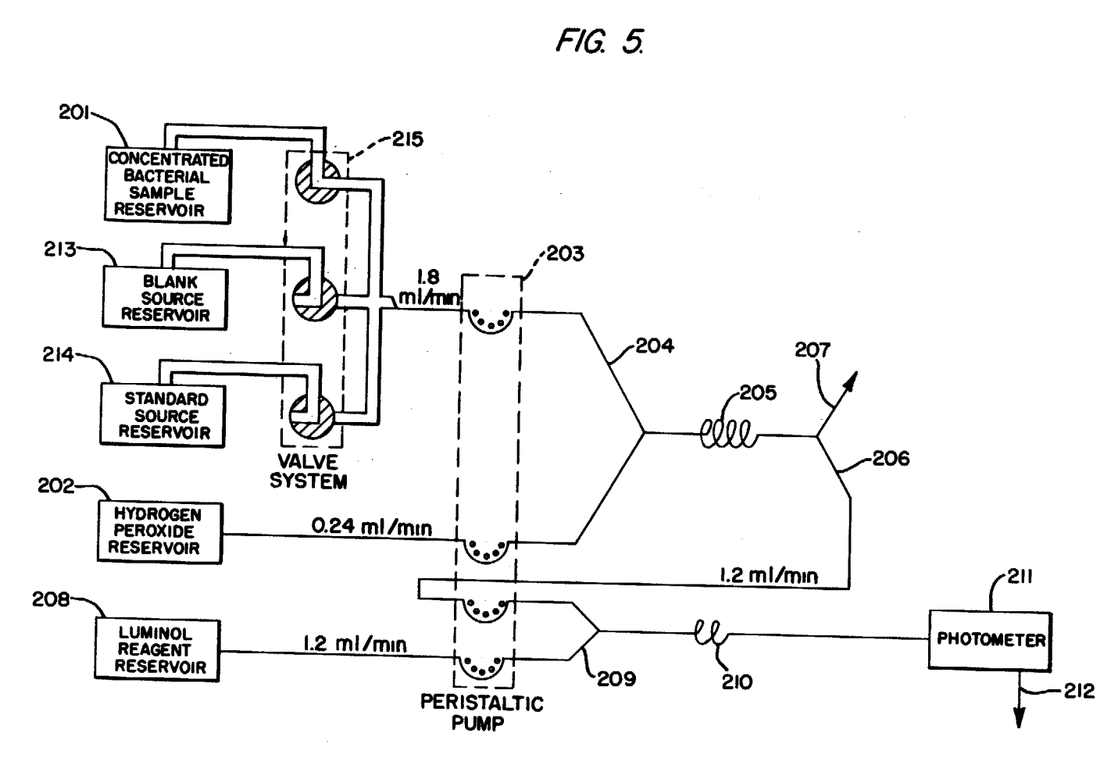
FIG. 5 is a block diagram depicting the automated iron porphyrin assay configuration of the invention.

FIG. 5 discloses an embodiment of an automatic system for carrying out a chemiluminescent assay of bacterial iron porphyrin in a fluid. A concentracted bacterial sample reservoir 201, a blank reservoir 213, and a bacterial standard reservoir 214 are all connected to one channel of a peristaltic pump 203 via a valve system 215. These three reservoirs are sequentially switched into the overall system for individual iron porphyrin assay. The concentrated bacterial sample reservoir 201 is drawn from the concentration reservoir 50 as shown in FIG. 3B after completion of the last cycle. The blank reservoir 213 is the filtrate drawn from the filtrate reservoir 51 as shown in FIG. 3B after completion of the last cycle. The standard is a known number of bacterial cells, for example, E. coli, usually approximately $10^7$ cells/ml as established by a Coulter counter. The standard is an overnight *E. coli* culture in trypticase soy broth diluted in sterile, deionized water. The system may be operated continuously or periodically.

The blank is normally first to be assayed. The blank source reservoir 213 is switched into the system via valve system 215 which allows the peristaltic pump 203 to begin drawing the fluid. At the same time the same peristaltic pump is drawing a 3% solution of hydrogen peroxide from a hydrogen peroxide reservoir 202. As with all peristaltic pump configurations, the speed of the pump and the diameter of the tubing connecting the fluid source to the pump are designed to permit the desired fluid flow rates. In this case, the fluid being assayed flows at the rate of 1.8 ml/min. and the hydrogen peroxide flows at 0.24 ml/min. The two flows are combined in a "Y" junction connector 204 and enter a residence coil 205 for a period of 2 minutes. The combined fluid then flows into "Y" junction connector 206. Sufficient fluid drops out of drain leg 206 to allow the remaining fluid to flow into still another channel of peristaltic pump 203 at a rate of 1.2 ml/min. At the same time, 1.2 ml/min. of luminol reagent ($2.5 \times 10^{-4}$ M luminol, $6.33 \times 10^{-3}$ M EDTA, 0.1% $H_2O_2$ in 0.75 N NaOH) from a luminol reagent reservoir 208 is drawn through yet another channel of the peristaltic pump 203 and mixed with the combined fluid through use of a "Y" junction connector 209. The output of the "Y" junction connector 209 runs through a residence coil 210 for a period of six seconds. Thereafter, the fluid flows through a photometer 211 for continuous light readings and out of the system through a photometer drain 212. The standard source reservoir 214 and the cncentrated bacterial sample reservoir are thereafter switched in and assays taken in a similar fashion.

The system disclosed, therefore, mixes either the concentrated bacterial sample, the blank or the standard with hydrogen peroxide for a period of 2 minutes to allow soluble iron porphyrins to be degraded for the purpose of eliminating false readings they would produce. The sample-hydrogen peroxide mix is then mixed with the luminol reagent for a period of six seconds before passage through a photometer. This six second delay results in the measurement of the light reaction caused only by the luminol and bacterial iron porphyrins, and not by short-lived signals from inorganic sources.

The blank reading is subtracted from the bacterial sample reading and compared with the reading for the standard on a simple ratio basis.

The invention is further illustrated by the following examples in which all parts and percentages are by weight unless otherwise indicated. The examples are illustrative of results obtained with various embodiments of the invention and are provided to teach those skilled in the art how to practice the invention and to represent given modes for carrying out the invention.

EXAMPLE I

This example involves a procedure for concentrating the bacteria contained in a 10 liter wastewater effluent sample 100-fold by using a hollow fiber filter/concentrator in a recirculation mode.

a. A hollow fiber filter cncentrator, pump and water container was set up in a recirculation mode. The straws of the filter provided a filter area of 1000 $cm^2$ with a 50,000 Mol. Wt. cut-off.

b. A 10 liter wastewater sample was placed in the container and pumped at the rate of about 50 ml per minute for a period of about 3 hours until only 100 ml and most of the bacteria remained in the container.

EXAMPLE II

This example involves a procedure for concentrating the bacteria contained in a 10 liter wastewater sample 100-fold by using a hollow fiber filter/concentrator in a blocked mode.

a. A hollow fiber filter/concentrator, pump and container was set up in a blocked mode. The straws of the filter provided a filter area of 10,000 $cm^2$ with a 50,000 Mol. Wt. cut-off.

b. A 10 liter wastewater sample was placed in the container and pumped through the straws at the rate of about 600 ml per minute for a period of about 20 minutes until the volume in the container was reduced to essentially zero and the bacteria were contained on the inner surfaces of the straws.

c. The filter/concentrator was switched to a backwash mode and 100 ml of deionized water was backwashed across the straws.

d. The filter/concentrator was switched back to a concentration mode and operated until a zero volume condition occurred once again.

e. Steps "c" and "d" were repeated two and a half times whereby "c" was the last repeated step, resulting in the bacteria being concentrated in a 100 ml. volume and collected in the container.

EXAMPLE III

This example involves a procedure for concentrating the bacteria contained in a 10 liter wastewater sample 100-fold by using a hollow fiber filter/concentrator in a combination recirculation and backwash mode.

a. A hollow fiber filter/concentrator, pump and water container were set up in a recirculation mode. The straws of the filter provided a filter area of 1,000 $cm^2$ with a 50,000 Mol. Wt. cut-off.

b. A 10 liter wastewater sample was placed in the container and pumped until the volume in the container was reduced to essentially zero and the bacteria were contained on the inner surfaces of the straws.

c. The filter/concentrator was switched to a backwash mode and 100 ml of deionized water was backwashed across the straws, the 100 ml being collected in the container.

EXAMPLE IV

This example involves a procedure for the rapid assay of bacteria in a wastewater effluent sample employing firefly luciferase-ATP assay-injection methodology.

a. 0.15 ml of 0.6 $NHNO_3$ was added to 1.2 ml of wastewater effluent (which was not concentrated since it was suspected of containing a high number of bacteria).

b. The nitric acid-sample mix was allowed to stand for a period of one minute to allow sufficient time for cell rupture.

c. The sample was diluted 1:1 by adding 1.35 ml of sterile, deionized water.

d. 0.1 ml of the resulting sample was injected into a container containing a 0.1 ml luciferase-luciferin mixture and the resulting bioluminescent reaction was measured by a photometer at 0.30 light units.

e. A blank was developed by filtering wastewater through a 0.22$\mu$ cellulose filter. 1.2 ml of the filtered wastewater was processed through steps "a" through "d", obtaining a reading of 0.09 light units.

f. A standard was developed by taking 1.2 ml of 0.1 μg ATP/ml in deionized water through steps "a" through "d" obtaining a reading of 3.9 light units.

g. The sample under examination was calculated to have an ATP concentration of $5.38 \times 10^{-3}$ μg ATP/ml through the following equation:

$$\frac{\text{sample reading} - \text{blank reading}}{X} = \frac{\text{standard reading}}{\text{standard } ATP \text{ concentration}}$$

$$\frac{0.3 - 0.09}{X} = \frac{3.9}{0.1 \text{ μg } ATP/ml}$$

$$\frac{(0.3 - 0.09) \times 0.1 \text{ μg } ATP/ml}{3.9} = X$$

$$X = 5.38 \times 10^{-3} \text{ μg } ATP/ml$$

h. The bacteria concentration in the sample was calculated by using an average concentration figure of ATP/cell in bacteria of $3 \times 10^{-10}$ μg ATP/cell. It was determined that the sample had a bacterial concentration of $1.83 \times 10^7$ cells/ml by use of the following equation.

$$\frac{\text{μg } ATP/ml \text{ sample}}{\text{μg } ATP/\text{cell}} = \text{cells/ml}$$

$$\frac{5.38 \times 10^{-3}}{3 \times 10^{-10}} = 1.83 \times 10^7 \text{ cells/ml}$$

EXAMPLE V

This example involves a procedure for the rapid assay of cells in a wastewater sample employing luminol-iron porphyrin assay-injection methodology.

a. 1.0 ml of 3% hydrogen peroxide was added to 6.0 ml of sample and the mixture was allowed to stand for 2 minutes.

b. 0.15 ml of the mixture was immediately injected into a container containing 0.15 ml of luminol reagent and the chemiluminescent reaction was measured by a photometer at 14.7 light units.

c. A blank was developed by filtering wastewater through a 0.22 micron cellulose filter. 6.0 ml of the filtered wastewater was processed through steps "a" and "b", obtaining a reading of 0.15 light units.

d. A standard was developed by taking an overnight culture of E. coli in trypticase soy broth, which was centrifuged at 10,000 RCF×G for 10 minutes and suspending the bacterial pellet in a volume of sterile, deionized water equal to one hundred times the original volume of the trypticase soy broth. A Coulter particle count was obtained and then a 6.0 ml portion was processed through steps "a" and "b". The Coulter particle count was $1.69 \times 10^7$ cells/ml and the photometer reading was 6.0 light units.

e. The sample under examination was calculated to have a total cell concentration of $4.11 \times 10^7$ cells/ml through use of the following equation:

$$\frac{\text{sample reading} - \text{blank reading}}{X} = \frac{\text{standard reading}}{\text{Coulter particle count}}$$

$$\frac{14.7 - 0.15}{X} = \frac{6.0}{1.69 \times 10^7 \text{ cells/ml}}$$

$$\frac{(14.7 - 0.15) \times 1.69 \times 10^7 \text{ cells/ml}}{6.0} = X$$

$$X = 4.11 \times 10^7 \text{ cells/ml}$$

EXAMPLE VI

This example involves a procedure for the rapid assay of cells in a wastewater sample employing a modified luminol iron porphyrin assay-injection methodology which allows differentiation between viable and dead cells.

a. Carbon monoxide was bubbled through 10 ml of sample for a 20 minute period.

b. 0.15 ml of the bubbled sample was immediately injected into a container containing 0.15 ml of luminol reagent and the chemiluminscent reaction measured by a photometer was 6.0 light units. (This relates to dead cells present).

c. 0.15 ml of the sample, without bubbling, was immediately injected into a container containing 0.15 ml of luminol reagent and the chemiluminescent reaction measured by a photometer was 14.7 light units. (This relates to total cells present.)

d. A blank and a standard were developed as set forth in steps "c" and "d" of Example V without the use of hydrogen peroxide in step "a". The blank was 0.15 light units and the standard was 6.0 light units.

e. The sample under examination was calculated to have a total cell concentration of $4.11 \times 10^7$ cells/ml and a viable cell percentage of 60%. The total was determined through use of the equation set forth in Example V, step e. The viable cell percentage is calculated through the following equation.

$$1 - \frac{(\text{sample reading w/CO bubbling} - \text{blank reading})}{(\text{sample reading w/o CO bubbling} - \text{blank reading})} \times 100 = \% \text{ viable cells}$$

$$1 - \frac{(6.0 - 0.15)}{(14.7 - 0.15)} \times 100 = 60\% \text{ viable cells}$$

EXAMPLE VII

This example involves a procedure for the rapid assay of ATP in microorganisms contained in an aquatic environment as a relative indication of biomass. This example employs a methodology useful for samples from waters exhibiting a substantial degree of salinity.

a. The microorganisms in a 100 ml sample were concentrated on a 0.22μ vacuum filter and the filtrate retained.

b. 10.0 ml of N $HNO_3$ was applied to the filter and allowed to stand for a period of one minute.

c. The acid was pulled through the filter to extract the ATP from the microorganisms. The extract was collected in a test tube.

d. The extract was then diluted 1/20 by adding 0.5 ml of the extract to 9.5 ml of sterile, deionized water.

e. The diluted extract was assayed by injecting 0.1 ml of the extract into 0.1 ml luciferase-luciferin solution contained in a container and the light output measured by a photometer. A reading of 0.49 light units was obtained.

f. A blank was developed by passing the filtrate through a new filter and repeating steps "b" through "e". A reading of 0.086 light units was obtained.

g. A standard was developed by first flushing filtrate through a new filter, then flushing a solution of $10^{-2}$ μg ATP/ml in 1 N HNO₃ through the filter, thereafter repeating steps "d" and "e". A reading of 12.3 light units was obtained.

h. The ATP content of the sample, indicating the relative biomass contained in the sample was obtained by the following equation.

$$\frac{\text{standard } ATP \text{ concentration}}{\text{standard reading}} = \frac{\text{sample } ATP \text{ concentration}}{\text{sample reading} - \text{blank reading}}$$

$$\frac{10^{-2} \, \mu\text{gm } ATP/\text{ml.}}{12.3} = \frac{\text{sample } ATP \text{ concentration}}{0.49 - 0.086}$$

$$\text{sample } ATP \text{ concentration} = \frac{(10^{-2} \, \mu\text{gm } ATP/\text{ml.}) \times 0.41}{12.3}$$

$$\text{sample } ATP \text{ concentration} = 3.4 \times 10^{-4} \, \mu\text{gm } ATP/\text{ml.}$$

EXAMPLE VIII

This example involves a procedure for the rapid assay of iron porphyrins in microorganisms contained in an aquatic environment as a relative indication of biomass. This example employs a methodology useful for samples from water exhibiting a substantial degree of salinity.

a. The microorganisms in a 1.0 ml. sample were concentrated on a 0.22 u vacuum filter (Gelman ACROPORE) and the filtrate retained.

b. 1.0 ml of 0.1 N NaOH—50% ethanol was added to the filter and allowed to stand for a period of 1 minute.

c. The extract containing iron porphyrins was pulled through the filter by vacuum and collected in a test tube.

d. 0.15 ml. of the extract was injected into a container containing 0.15 ml. luminol reagent and the light output read by a photometer after a 6 second delay from the time of injection. A reading of 3.3 light units was obtained.

e. A blank was developed by passing the filtrate through a new filter and repeating steps "b" through "d". A reading of 0.1 light units was obtained.

f. A standard was developed by preparing a iron porphyrin solution of $2.48 \times 10^{-2}$ µg catalase/ml 0.1 N NaOH—50% ethanal (freshly prepared), and processed as in step "d". A photometer reading of 9.5 light units was obtained.

g. The sample under examination was calculated to have a total/iron porphyrin concentration of $8.35 \times 10^{-3}$ µg catalase units/ml by use of the following equation.

$$\frac{\text{sample reading} - \text{blank reading}}{X} = \frac{\text{standard reading}}{\text{standard catalase concentration}}$$

$$\frac{3.3 - 0.1}{X} = \frac{9.5}{2.48 \times 10^{-2} \, \mu\text{g catalase/ml}}$$

$$X = \frac{(3.3 - 0.1) \, 2.48 \times 10^{-2} \, \mu\text{g catalase/ml}}{9.5}$$

$$X = 8.35 \times 10^{-3} \, \mu\text{g catalase units/ml}$$

The methods and apparatus of the instant invention, as disclosed herein, provide significant improvements in concentrating bacteria and in quantitatively detecting bacteria or microbial biomass in water generally and wastewater effluent or sea water in particular.

The principles, preferred embodiments, advantages and operation of the present invention have been described herein. The invention which is intended to be protected herein, however, is not to be construed as limited to the particular forms and methods disclosed because these are to be regarded as illustrative rather than restrictive. Variations and changes may be made by those skilled in the art without departing from the spirit of the present invention.

What is claimed is:

1. A method for the rapid assay of bacteria containing iron porphyrins in a water sample comprising treating said sample by:
   a. bubbling carbon monoxide through a portion of said water sample;
   b. adding an aliquot of said sample portion to luminol reagent;
   c. measuring the emitted light level;
   d. adding another aliquot of said sample portion to luminol reagent;
   e. measuring the emitted light level;
   f. developing a blank by removing bacteria from yet another portion of said water sample;
   g. adding an aliquot of said blank to luminol reagent;
   h. measuring the emitted light level;
   i. developing a standard by a bacterial culture followed by a conventional bacterial count;
   j. adding an aliquot of said standard to luminol reagent;
   k. measuring the emitted light level; and
   l. calculating the bacteria concentration in the sample.

2. The method of claim 1 wherein said water sample undergoes bacterial concentration prior to said carbon monoxide bubbling.

3. The method of claim 2 wherein said bacterial concentration is accomplished by a hollow fiber membrane.

4. A method for the rapid assay of bacteria containing adenosine triphosphate in a water sample consisting essentially of treating said sample by:
   a. rupturing bacterial cells in a portion of said water sample, thereby releasing adenosine triphosphate;
   b. diluting the treated portion of said water sample by the addition of sterile, deionized water;
   c. adding an aliquot of the portion of said water sample to a luciferase-luciferin solution;
   d. measuring the emitted light level;
   e. developing a blank by removing bacteria from another portion of said water sample;
   f. treating said blank as if to rupture bacterial cells;
   g. diluting said blank by the addition of sterile, deionized water;
   h. adding an aliquot of said blank to a luciferase-luciferin solution;
   i. measuring the emitted light level;
   j. developing a standard by adding a known amount of ATP to sterile, deionized water;
   k. treating said standard as if to rupture bacterial cells;
   l. diluting said standard by the addition of sterile, deionized water;
   m. adding an aliquot of said standard to a luciferase-luciferin solution;
   n. measuring the emitted light level;
   o. calculating the adenosine triphosphate concentration; and
   p. calculating the bacteria concentration.

5. The method of claim 4 wherein said water sample is prefiltered prior to said bacterial cell rupture.

6. The method of claim 4 wherein said water sample undergoes bacterial concentration prior to said bacterial cell rupture.

7. The method of claim 6 wherein said bacterial concentration is accomplished by a hollow fiber membrane.

8. The method of claim 4 wherein said water sample is prefiltered and undergoes bacterial concentration prior to said bacterial cell rupture.

9. The method of claim 8 wherein said bacterial concentration is accomplished by a hollow fiber membrane.

10. A method for measuring adenosine triphosphate in a water sample and thereby determining bacterial concentration consisting essentially of
   a. forming reservoirs of a water sample, a blank, a standard, an acid, a luciferase-luciferin mixture, and sterile, deionized water;
   b. pumping said water sample and said acid and thereafter mixing same for a predetermined period of time;
   c. pumping said water sample—acid mixture and said sterile, deionized water and thereafter mixing same;
   d. pumping said water sample—acid—sterile, deionized water mixture and said luciferase-luciferin mixture and thereafter mixing same and measuring the emitted light level;
   e. pumping said blank and said acid and thereafter mixing same for said predetermined period of time;
   f. pumping said blank—acid mixture and said sterile, deionized water and thereafter mixing same;
   g. pumping said blank—acid—sterile, dionized water mixture and said luciferase-luciferin mixture and thereafter mixing same and measuring the emitted light level;
   h. pumping said standard and said acid and thereafter mixing same for said predetermined period of time;
   i. pumping said standard—acid mixture and said sterile, deionized water and thereafter mixing same;
   j. pumping said standard—acid—sterile, deionized water mixture and said luciferase-luciferin mixture and thereafter mixing same and measuring the emitted light level; and
   k. calculating the bacterial concentration.

11. The method of claim 10 wherein all said pumping is accomplished by a plurality of peristaltic pump channels.

12. The method of claim 10 wherein each of said predetermined periods of time is 60 seconds.

13. The method of claim 10 wherein said water sample is prefiltered prior to said water sample reservoir formation.

14. The method of claim 10 wherein said water sample undergoes bacterial concentration prior to said water sample reservoir formation.

15. The method of claim 14 wherein said bacterial concentration is accomplished by a hollow fiber membrane.

16. The method of claim 10 wherein said water sample is prefiltered and undergoes bacterial concentration prior to said water sample reservoir formation.

17. The method of claim 16 wherein said bacterial concentration is accomplished by a hollow fiber membrane.

18. A bioluminescent method for rapidly assaying bacteria in a water sample by detecting adenosine triphosphate in the water sample without first removing non-bacterial sources of adenosine triphosphate consisting essentially of treating the sample by:
   (a) rupturing bacterial cells in a portion of the sample, diluting the portion by the addition of a sterile water, adding an aliquot of the portion to a luciferase-luciferin mixture and measuring the emitted light level;
   (b) developing a blank and measuring the emitted light level;
   (c) developing a standard and measuring the emitted light level; and
   (d) calculating the bacteria concentration.

19. The method of claim 18 wherein bacteria are concentrated prior to bacterial cell rupture.

20. The method of claim 18 wherein said blank employs sterile water and nitric acid.

21. The method of claim 18 wherein the standard employs pure ATP diluted in water.

22. A method for the rapid assay of bacteria containing iron porphyrins in a water sample comprising treating said sample by:
   a. adding hydrogen peroxide to a portion of said water sample and allowing the mixture to stand;
   b. adding an aliquot of said mixture to luminol reagent;
   c. measuring the emitted light level;
   d. developing a blank by removing bacteria from another portion of said water sample;
   e. treating said blank by adding hydrogen peroxide;
   f. adding an aliquot of said blank to luminol reagent;
   g. measuring the emitted light level;
   h. developing a standard by a bacterial culture followed by a bacterial count;
   i. treating said standard by adding hydrogen peroxide;
   j. adding an aliquiot of said standard to luminol reagent;
   k. measuring the emitted light level; and
   l. calculating the bacteria concentration.

23. The method of claim 22 wherein the emitted light level measurements of steps "c" and "g" are made after a 6 second delay.

24. The method of claim 22 wherein said water sample undergoes bacterial concentration prior to said hydrogen peroxide addition of step "a."

25. The method of claim 24 wherein said bacterial concentration is accomplished by a hollow fiber membrane.

26. A method for the rapid assay of iron porphyrins in microorganisms contained in a water sample comprising treating said sample by:
   a. concentrating the microorganisms on a filter and retaining the filtrate;
   b. adding a sodium hydroxide-ethanol mixture to said filter and allowing said mixture to stand for a period of time sufficient to extract iron porphyrins from the microorganisms;
   c. collecting said sodium hydroxide-ethanol-iron porphyrin extract
   d. assaying said extract by mixing a portion of said extract with luminol reagent and measuring the emitted light level;
   e. developing a blank by passing a portion of said filtrate through a new filter;
   f. adding a sodium hydroxide-ethanol mixture to said new filter and allowing it to stand for a period of time sufficient for extraction of iron porphyrins, thereby simulating an extract;

g. collecting said blank;

h. assaying said blank by mixing a portion of said simulated extract with luminol reagent and measuring the emitted light level;

i. developing a standard by a bacterial culture followed by a conventional bacteria count;

j. assaying said standard by mixing a portion of said standard with luminol reagent and measuring the emitted light level; and k. calculating the bacteria concentration in said sample.

27. The method of claim 26 wherein said sodium hydroxide-ethanol mixture is a 0.1 N NaOH—50% ethanol solution.

28. The method of claim 26 wherein all the emitted light levels are measured about six seconds after injection into said luminol reagent.

29. A method for measuring iron porphyrins in a water sample and thereby determining bacterial concentration, comprising:

a. forming reservoirs of a water sample, a blank, a standard, a hydrogen peroxide solution and luminol reagent;

b. pumping said water sample and said hydrogen peroxide solution and thereafter mixing same for a first predetermined period of time;

c. pumping said water sample—hydrogen peroxide solution mixture and said luminol reagent and thereafter mixing same for a second predetermined period of time and measuring the emitted light level;

d. pumping said blank and said hydrogen peroxide solution and thereafter mixing same for a first predetermined period of time;

e. pumping the blank—hydrogen peroxide solution mixture and luminol reagent and thereafter mixing same for a second predetermined period of time and measuring the emitted light level;

f. pumping said standard and said hydrogen peroxide solution and thereafter mixing same for a first predetermined period of time;

g. pumping said standard—hydrogen peroxide solution mixture and said luminol reagent and thereafter mixing same for a second predetermined period of time and measuring the emitted light level; and h. calculating the bacterial concentration.

30. The method of claim 29 wherein said pumping is accomplished by a plurality of peristaltic pump channels.

31. The method of claim 29 wherein said first predetermined period of time is 2 minutes.

32. The method of claim 29 wherein said second predetermined period of time is 6 seconds.

33. The method of claim 29 wherein said water sample is prefiltered prior to said water sample reservoir formation.

34. The method of claim 29 wherein said water sample undergoes bacterial concentration prior to said water sample reservoir formation.

35. The method of claim 34 wherein said bacterial concentration is accomplished by a hollow fiber membrane.

36. The method of claim 29 wherein said water sample is prefiltered and undergoes bacterial concentration prior to said water sample reservoir formation.

37. The method of claim 36 wherein said bacterial concentration is accomplished by a hollow fiber membrane.

38. A chemiluminescent method for rapidly assaying bacteria in a water sample by detecting iron porphyrins in the water sample comprising treating the sample by:

(a) first adding hydrogen peroxide to a portion of said water sample, then adding an aliquot of the sample to luminal reagent, and measuring the emitted light level;

(b) developing a blank and measuring the emitted light level;

(c) developing a standard and measuring the emitted light level; and (d) calculating the bacteria concentration.

39. The method of claim 38 wherein bacteria are concentrated prior to treatment of the sample with hydrogen peroxide.

40. The method of claim 38 wherein said blank is deionized water.

41. The method of claim 38 wherein said standard is a known amount of bacteria in deionized water.

42. The method of claim 38 wherein emitted light measurements are taken after a six second delay.

43. A chemiluminescent method for rapidly assaying biomass contained in a saline water sample comprising treating the sample by;

(a) filtering the biomass in the sample and retaining both the biomass on the filter and the filtrate, adding a sodium hydroxide-ethanol mixture to the filter and collecting the extract, mixing the extract with luminol reagent and measuring the emitted light level;

(b) developing a blank and measuring the emitted light level;

(c) developing a standard and measuring the emitted light level; and (d) calculating the biomass concentration.

44. The method of claim 43 wherein said blank employs the filtrate of the saline water followed by extraction with a sodium hydroxide-ethanol solution.

45. The method of claim 43 wherein said standard employs a known amount of catalase which has been added to a sodium hydroxide-ethanol solution.

* * * * *